United States Patent
Kadziauskas et al.

(10) Patent No.: US 6,887,209 B2
(45) Date of Patent: May 3, 2005

(54) PULSED VACUUM AND/OR FLOW METHOD AND APPARATUS FOR TISSUE REMOVAL

(75) Inventors: Kenneth E. Kadziauskas, Coto de Caza, CA (US); Paul W. Rockley, Laguna Niguel, CA (US); Mark S. Cole, Trabuco Canyon, CA (US)

(73) Assignee: Advanced Medical Optics, Santa Ana, CA (US)

( * ) Notice: Subject to any disclaimer, the term of this patent is extended or adjusted under 35 U.S.C. 154(b) by 97 days.

(21) Appl. No.: 10/073,372

(22) Filed: Jan. 25, 2002

(65) Prior Publication Data

US 2003/0144606 A1 Jul. 31, 2003

(51) Int. Cl.[7] ............................................. A61B 10/00
(52) U.S. Cl. ....................... 600/565; 600/566; 600/567; 600/568; 606/107; 606/171
(58) Field of Search ................................. 606/115, 107, 606/171; 600/562, 564, 565, 566, 567, 568, 571

(56) References Cited

U.S. PATENT DOCUMENTS

| | | | |
|---|---|---|---|
| 3,884,238 A | * | 5/1975 | O'Malley et al. ............ 606/107 |
| 4,203,444 A | | 5/1980 | Bonnell et al. |
| 4,598,710 A | | 7/1986 | Kleinberg et al. |
| 4,662,869 A | * | 5/1987 | Wright ......................... 604/22 |
| 4,696,298 A | | 9/1987 | Higgins et al. |
| 4,819,635 A | | 4/1989 | Shapiro |
| 4,850,354 A | | 7/1989 | McGurk-Burleson et al. |
| 4,909,249 A | | 3/1990 | Akkas et al. |
| 5,106,364 A | | 4/1992 | Hayafuji et al. |
| 5,176,628 A | | 1/1993 | Charles et al. |
| 5,284,472 A | | 2/1994 | Sussman et al. |
| 5,685,320 A | * | 11/1997 | Zimmon et al. ............. 600/567 |
| 6,017,316 A | * | 1/2000 | Ritchart et al. ............. 600/567 |
| 6,120,462 A | * | 9/2000 | Hibner et al. ................ 600/566 |
| 2002/0082519 A1 | * | 6/2002 | Miller et al. ................. 600/566 |

* cited by examiner

Primary Examiner—Max F. Hindenburg
Assistant Examiner—Jonathan Foreman
(74) Attorney, Agent, or Firm—Walter A. Hackler

(57) ABSTRACT

A method of controlling a surgical cutting device, the device including a hollow needle with a port for tissue entry and a moveable cutting blade for severing tissue entering the needle through the port, the blade being movable between a first portion enabling tissue entry through the port and a second portion closing the port, the tissue entering the needle being severed as the blade moves between the first and second portions, the method includes the steps: a) providing vacuum to the hollow needle to cause tissue entry into the needle through the port; b) moving the blade from the first portion to the second position to sever the tissue entering the needle; c) evacuating severed tissue from the needle by vacuum; d) reducing vacuum to the needle before moving the blade from the second position to the first position; and repeating steps (a) through (d).

1 Claim, 2 Drawing Sheets

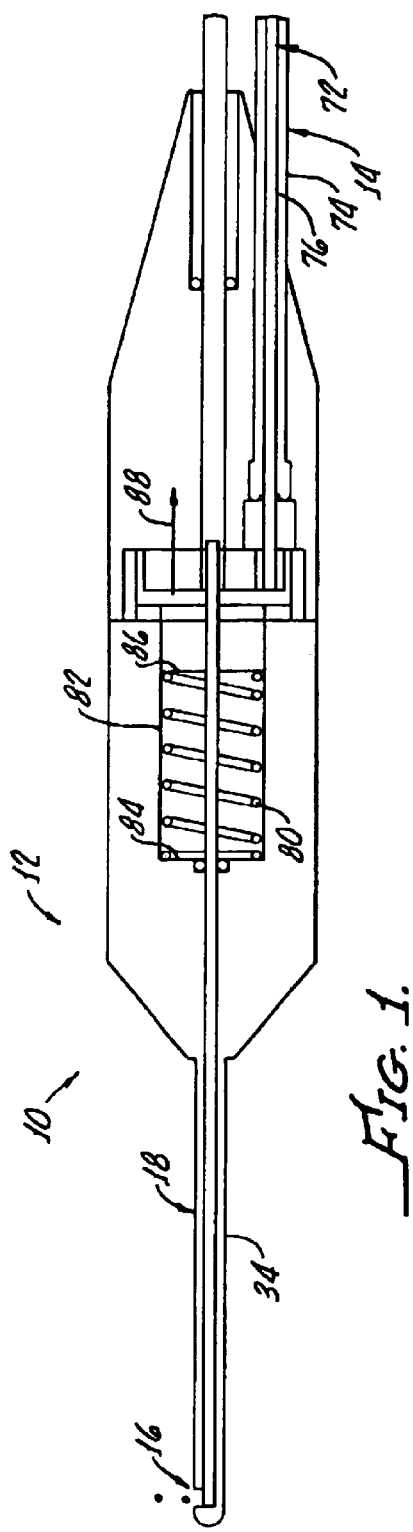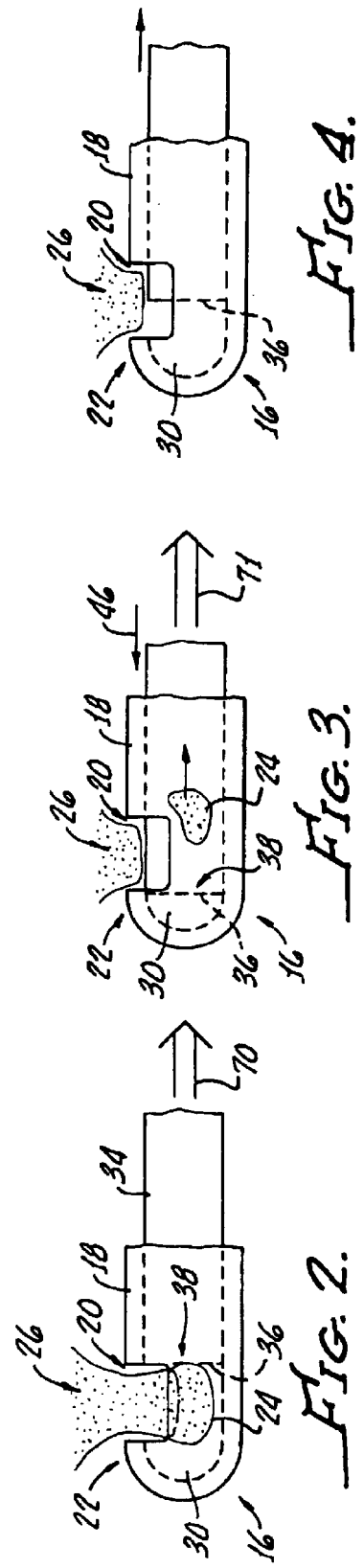

PULSED VACUUM AND/OR FLOW METHOD AND APPARATUS FOR TISSUE REMOVAL

The present invention generally relates to surgical instruments and more particularly relates to a tissue cutting surgical device suitable for use in vitreous and retinal surgery.

An eye surgery procedure performed behind the lens is called vitreous surgery in as much as the posterior chamber of the eye is filled with a transparent jelly called the vitreous humor ("vitreous").

Understandably, vitreous surgery, as with any ophthalmic surgical procedure, requires great precision. The vitreous is filled with numerous fiber like materials, some of which are attached to the delicate retina. The presence of these fibers make vitreous surgery quite difficult, due to the possibility of retinal injury occurring if one of these fibers inadvertently severed.

Moreover, retinal surgery, which involves actual cutting of the retina of the eye, must be performed with even greater precision, as the retina is the immediate instrument of vision and is directly connected with the brain by the optic nerve. Thus, a surgical instrument suitable for use in vitreous surgery may not be suitable for use in retinal surgery.

For example, a state of the art vitreous cutter may comprise a hand held probe having a cutting tip thereon. The cutting tip comprises an outer tube having a perforation therein, and an inner tube having a reciprocating cutting edge or blade for shearing portions of tissue drawn into the outer tube perforation. The inner tube is typically driven in an axially reciprocating fashion, at a cutting rate of about 400–2000 strokes per minute, by pneumatic means. More particularly, the pneumatic means typically includes a pressurized air source which supplies periodic bursts of air that drive the inner tube forward within the outer tube. A diaphragm or spring is included in the probe which biases the inner cutting tube backward to a home position. Thus, the cutting strokes of the inner tube are controlled by periodic bursts of air forcing the inner cutting tube forward, alternating with the discontinuing thereof such that the biased spring forces the cutting tube backward.

It is well known that such pneumatically driven devices do not operate effectively at very low speeds and are designed for operation at high speeds, for example, hundreds of cycles per minute. Moreover, although the cutting rate provided by such instruments may be controllable to some extent, control over speed and length of an individual cutting stroke is not obtainable. Thus, such cutters may be inappropriate for use in retinal surgery, which requires exceptional precision and control in order to avoid serious injury to the patient.

Other tissue cutters have utilized mechanical means for driving the stroking motion of a blade at a selected stroke rate of down to about one stroke per minute, or in other words, at an exceptionally slow rate. This enables, a physician to control amount and rate of individual strokes of the stroking motion down to even a fraction of a cut, if so desired.

Such hereinabove described tissue cutters also require an aspiration, or vacuum line, in fluid communication with a bore from a cutter's sleeve for both drawing a portion of tissue into the cutter, and subsequently, removing a cut portion of tissue from cutter.

The present invention is directed to control of such aspiration or vacuum. This method manages the pressure across a tissue cutter for causing controlled amounts, or "packets", of material to enter the cutter for cutting or processing.

SUMMERY OF THE INVENTION

In accordance with the present invention, surgical apparatus for cutting tissue is provided which includes a hollow needle having a port therein for enabling tissue entry into a needle lumen through the port. A cutting blade or edge disposed within the hollow needle is provided for severing tissue entering the needle lumen through the port.

A driver connected to the cutting blade is provided for moving the blade between a first position enabling tissue entry through the port and a second position closing the port, the tissue entering the needle being severed as the blade moves between the first and second position.

A vacuum source is provided and disposed in communication with the needle lumen for causing tissue entry into the lumen through the port and for aspirating, or evacuating severed tissue from the needle lumen.

A controller, including a valve for controlling vacuum communication between the vacuum source and the needle lumen and connected to the driver, is provided for coordinating vacuum/blade movement so that vacuum is provided to the needle lumen when the blade is in the first position and during severing tissue by the blade and reducing vacuum to the needle before moving the blade from the second position to the first position.

A method utilizing the hereinabove set forth apparatus includes providing vacuum to the hollow needle to cause tissue entry into the needle through the port and moving the blade from the first position to the second position to sever the tissue entering the needle.

The method further provides for evacuating, or aspirating severed tissue from the needle by vacuum and reducing the vacuum to the needle before moving the blade from the second position to the first position. These steps are repeated during the method.

More particularly, the vacuum applied to the hollow needle is regulated to control an amount of tissue entering the port before severing thereof by the blade. In addition, the step of reducing vacuum may include stopping the vacuum before moving the blade from the second position to the first position.

Still more particularly, in accordance with the present invention, the speed of the blade movement in moving between the first and second positions may be regulated to control the amounts of tissue severed during the blade movement. In combination therewith, the vacuum may be regulated to obtain a predictable bite, or severed amount of tissue, with a predictable amount of traction to pull the tissue in order to affect a cut. As a result, tractionless tissue removal may be possible with lower cut rates. This allows for three key factors in tissue processing to be separated for control: cut speed/rate; size of the bite removed in a cut; and the flow rate of tissue into the port. Cut speed may also refer to the rate of cuts per minute.

BRIEF DESCRIPTION OF THE DRAWINGS

The advantages and features of the present invention will be better understood by the following detailed description when considered in conjunction with the accompanying drawings in which:

FIG. 1 is a cross-sectional view of surgical apparatus in accordance with the present invention for cutting tissue which includes a hollow needle having a port therein for enabling tissue entry into a needle lumen through the port;

FIG. 2 illustrates a needle tip of the apparatus shown in FIG. 1 as a portion of tissue to be cut, or severed is being drawn into the port by vacuum in communication with the needle lumen;

FIG. 3 illustrates a severed portion of tissue being evacuated from the needle by vacuum aspiration;

FIG. 4 illustrates the reduction, or stoppage, of aspiration, or vacuum while the blade is retracted and partially covering the port.

DETAILED DESCRIPTION

Figure 5:
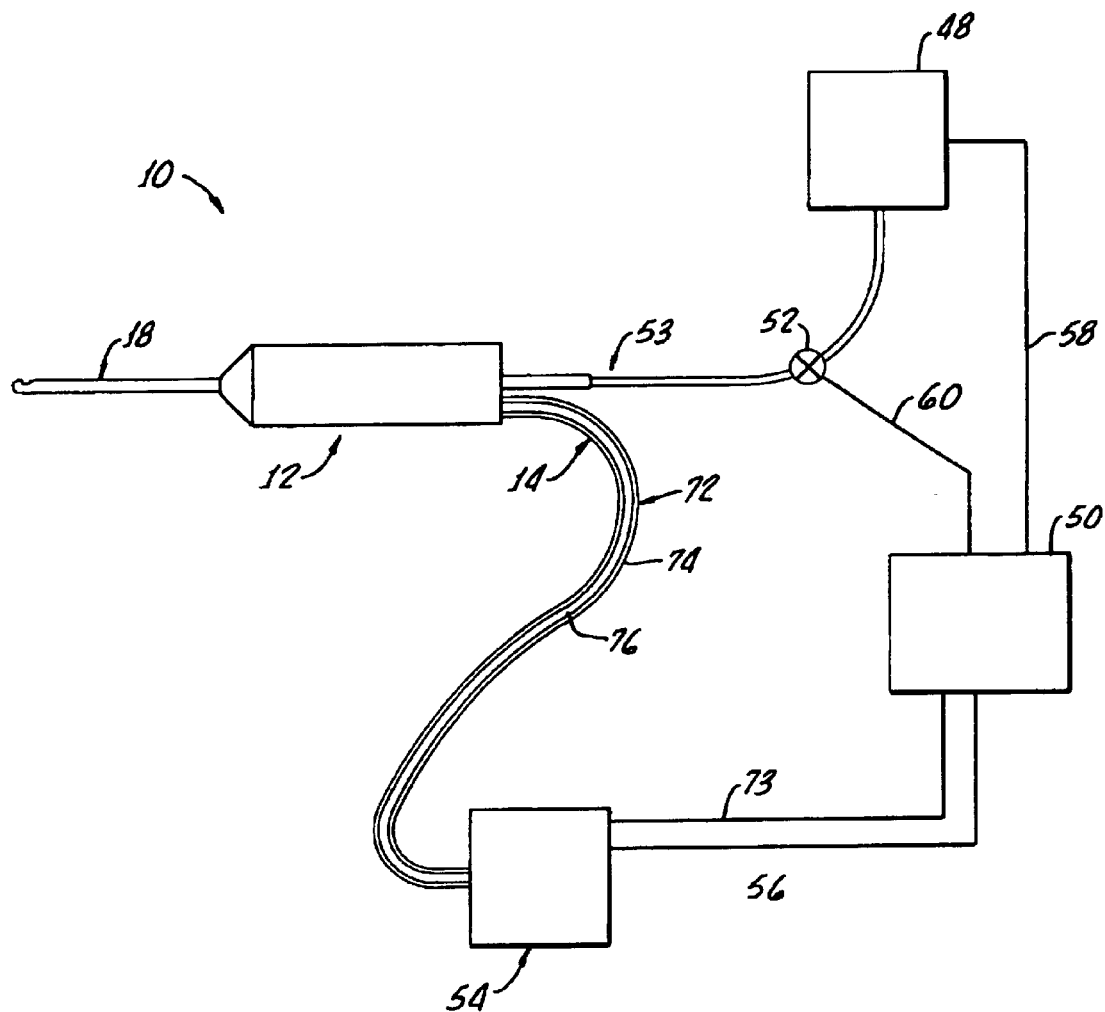
FIG. 5 shows a schematic diagram of the apparatus in accordance with the present.

Turning now to FIG. 1, there is shown surgical cutting apparatus 10, in accordance with the present invention, which generally includes a probe 12 as means for cutting tissue of a body (not shown in FIG. 1), and a driver 14 for causing the cutting action of the probe 12 as hereinafter described. It should be appreciated that the driver 14 is shown as a mechanical device for illustration purposes, alternate drivers, not shown, such as pneumatic drivers may be utilized.

More particularly, the probe 12 includes a needle 16 which is shown in detail in FIGS. 2–4. The needle 16 includes an outer sleeve 18 having an opening, or port 20, proximate a distal end 22 of the outer sleeve 18 as means for enabling entry of a portion 24 of tissue to be cut from the body 26 of tissue. The body 26 of tissue may be a vitreous humor of an eye, a retina of the eye, or any other body of tissue located in a confined area of a patient, such as to require the use of a narrow probe to access same.

The needle 16 is hollow and therefore contains a lumen 30. A cutter sleeve 34, coaxially disposed within the outer sleeve 18 and lumen 30 provides for shearing the portion 24 of tissue by a stroking motion thereof with respect to the outer sleeve 18. The cutter sleeve 34 includes a cutting edge or blade, 36 on a distal end 38 thereof which severs the portion 24 of tissue received through the port 20 as the cutter sleeve 34 is moved in the direction of arrow 46, see FIG. 3.

Although a simple coaxial sleeve cutting needle 16 is hereinabove described and shown in the drawings, other suitable probe tips of the shearing or scissor type, as are currently known in the art, (not shown) may be used with the present invention. Materials construction for the probe 12 and probe needle 16 may be of plastic or metal or combinations thereof, all suitable for use in surgical applications.

The driver 14 in combination with a vacuum source 48 and controller 50, see FIG. 5, enables a surgeon to use the probe 12 with maximum control over speed and length of tissue cuts. In other words, the stroking motion of the cutter sleeve 34 may be driven at a selected stroke rate from as slow as one or two strokes per minute, up to as fast as about two thousand strokes per minute, depending upon the particular surgical application. For example, for delicate retinal surgery, the cutter sleeve 34 may be driven at a very slow stroking rate, such that the physician has maximum control over each individual cut and can perform fractions of cuts if desired. On the other hand, for vitreous surgery where some or all of the vitreous is to be removed from the eye, a higher stroking rate may be preferable. Of course, a physician may alternate between high and low speeds in a single surgical procedure if desirable.

The controller 50 includes a shutter or pinch valve 52 disposed in a communication line 53 interconnecting the vacuum source 48 and the needle lumen 30. The driver 14 may include a stepper motor 54 which is regulated by the controller 50 through an interconnection 56. The controller, which may be of any suitable electrical type, controls the blade 36 position, vacuum source 48, and valve 52 via lines 58, 60 respectively.

In operation, as illustrated in FIGS. 2–4, vacuum, indicated by arrow 70 is provided to the hollow needle 16 to cause the tissue portion 24 to enter through the port 20, see FIG. 2, the blade 36 being in a first position enabling tissue 24 entry through the port 20, see FIG. 2.

The blade 36 is then moved to a second position closing the port 20 and severing the tissue portion 24. Continued vacuum, indicated arrow 71 as illustrated in FIG. 3 evacuates the tissue portions 24, from the lumen 30. Thereafter vacuum is reduced, or stopped, by the controller 50 through valve 52 before moving the blade 36 from the second position to the first position. The controller 50 may be provided an input signal corresponding to blade 36 position by a separate line 73 to the stepper motor 54. A separate sensor, not shown, may be utilized to generate the blade position signal as a function of time or such signal may be generated by the stepper 54.

By regulating blade 36 speed and position and vacuum through the controller 50 a fixed amount, or packet, of tissue 24 material enters the port 20 and is severed. Thus, tissue traction is minimized. Accordingly, the factors in tissue processing can be combined, namely, cut speed, bite size of tissue 24 removed in a cut and the flow rate of tissue into the port 20, and blade 36 position.

By way of specific example without limitation thereto the driver 14 may include a cable 72 which provides means for connecting the probe 12 and cutter sleeve 34 with blade 36 to the stepper motor 54 adapted to move the cutter sleeve 34 in the stroking motion. More particularly, the cable 72 may be a flexible coaxial cable comprised of an outer stationary cable 74 and an inner cable 76 slidably disposed therein.

The inner cable 76 is preferably mounted in an operative relationship with the cutter sleeve 34 such that an axial motion along a length of the inner cable 76 within the stationary outer cable 74 causes a complementary motion of the cutter sleeve 34. The cable 72 is connected to the stepper motor 54 is a conventional fashion such as to cause incremental sliding motions of the inner cable 76 in a highly controlled manner. Preferably, the stepper motor 54 is connected to the cable 72 such that the motor 54 drives the inner cable 76 in an incremental, pull and release fashion.

As shown in FIG. 1, the probe 12 may include a spring 80 therein as a means for biasing the cutter sleeve 34 against a pulling force applied thereto by the inner cable 76 and motor 54. For example, the spring 80 may be disposed in a chamber 82, and may be connected to a fixed wall 84 and a slidable wall 86 defining boundaries of the chamber 62.

More particularly, the cutter sleeve 34 and the inner cable 76 may be mounted in a conventional fashion to the slidable wall 86 such that the spring 80 biases the cutter sleeve 34 toward the distal end 22 of the outer sleeve 18, as shown in FIG. 3.

In operation, upon each controlled pull of the inner cable 76 by the motor 54, the slidable chamber wall 86 is forced in the direction of arrow 88, thus elongating, or stretching the spring 80 and moving the cutter sleeve 34 away from the distal end 22 to a right most position, such as shown in FIG. 2. The portion 24 of tissue is thus able to enter the port 20 within the outer sleeve 18, which may be aided by use of vacuums as hereinabove described. Subsequently, upon each controlled release, or discontinuing of pulling by the motor 54, the stretched spring 80 pulls the cutter sleeve 34 back toward the distal end 22, or home position, consequently cutting the portion 24 from the body 26 of tissue (FIG. 3). Repetitions of this operation enable cutting of a desired amount of tissue.

A gradual and steady release of pulling on the inner cable 76 by the stepper motor 54 in cooperation with a spring 80 operates to prevent uncontrollable rebounding motions of the cutter sleeve 34 when the device 10 is operated at slow speeds.

Through the controller 50, a physician is able to shear tissue at a stroke rate ranging from exceptionally slow speeds to very high speeds. When operated at a low speed, for example, one or two deliberate strokes per minute, the device 10 enables a physician to perform precise cuts or fractions of cuts with precision.

Although there has been hereinabove described a pulsed vacuum method and apparatus, in accordance with the present invention, for the purpose of illustrating the manner in which the invention may be used to advantage, it will be appreciated that the invention is not limited thereto. Accordingly, any and all modifications, variations, or equivalent arraignments which may occur to those skilled in the art should be considered to be within the scope of the invention as defined in the appended claims.

What is claimed is:

1. A surgical apparatus comprising:

a hollow needle having a port therein for enabling tissue entry into a needle lumen through said port;

a cutter sleeve including a cutting blade disposed within said hollow needle for severing tissue entering the needle lumen through said port;

a driver, connected to said cutting blade, for moving the blade between a first position enabling tissue entry through said port and a second position closing said port, the tissue entering the needle being severed as the blade moves between the first and second positions, said driver comprising a stepper motor and a cable for connecting said cutter sleeve for moving the cutter sleeve in a stroking motion, said cable including an outer stationary cable and an inner cable slidably disposed therein connected to said cutter sleeve;

a vacuum source in communication with said needle lumen for causing tissue entry into the needle lumen through said port and for aspiration of severed tissue through the lumen; and a controller, including a valve for controlling vacuum communication between said vacuum source and said needle lumen and connected to said driver, for coordinating vacuum and blade movement at rates between one communication and about 1000 communication per minute so that vacuum is provided to said needle lumen when the blade is in the first position and during severing of tissue by the blade and reducing vacuum to said needle lumen before moving the blade from the second position to the first position.

* * * * *